United States Patent [19]
Bruns et al.

[11] Patent Number: 5,984,678
[45] Date of Patent: *Nov. 16, 1999

[54] FRIABLE ABRASIVE MEDIA

[75] Inventors: Craig R Bruns; Thomas S. Blake; Mark S Fernwood, all of Danville, Calif.

[73] Assignee: Danville Engineering, San Ramon, Calif.

[ * ] Notice: This patent is subject to a terminal disclaimer.

[21] Appl. No.: 09/158,640

[22] Filed: Sep. 22, 1998

Related U.S. Application Data

[63] Continuation of application No. 08/647,686, May 13, 1996, Pat. No. 5,810,587.

[51] Int. Cl.$^6$ ..................................................... A61K 5/00
[52] U.S. Cl. ................................ 433/88; 433/216; 424/49
[58] Field of Search ....................... 433/88, 216; 51/309; 606/131; 424/49

[56] References Cited

U.S. PATENT DOCUMENTS

| | | | |
|---|---|---|---|
| 3,972,123 | 8/1976 | Black | 433/88 |
| 4,170,364 | 10/1979 | Cordon et al. | 424/49 |
| 4,174,571 | 11/1979 | Gallant | 433/88 |
| 4,519,811 | 5/1985 | Lalancette et al. | 51/309 |
| 4,759,774 | 7/1988 | Hochberg et al. | 51/309 |
| 4,776,794 | 10/1988 | Meller | 433/88 |
| 4,906,185 | 3/1990 | Randklev | 433/8 |
| 4,941,298 | 7/1990 | Fernwood et al. | 433/88 |
| 4,988,498 | 1/1991 | Evans et al. | 424/52 |
| 5,019,374 | 5/1991 | Raven | 424/52 |
| 5,032,383 | 7/1991 | Evans et al. | 424/49 |
| 5,096,702 | 3/1992 | Rolla et al. | 424/52 |
| 5,207,034 | 5/1993 | Lynn . | |
| 5,230,185 | 7/1993 | Kirschner et al. . | |
| 5,236,471 | 8/1993 | Van Dijen | 51/309 |
| 5,302,374 | 4/1994 | Wagner | 424/52 |
| 5,344,472 | 9/1994 | Lynn et al. | 451/75 |
| 5,356,292 | 10/1994 | Ho | 433/88 |
| 5,509,971 | 4/1996 | Kirschner | 51/309 |
| 5,601,430 | 2/1997 | Kutsch et al. | 433/215 |
| 5,810,587 | 9/1998 | Burns et al. | 433/88 |

OTHER PUBLICATIONS

Hawley's Condensed Chemical Dictionary, Van Nostrand Renhold Compnany, NY ©1996, p. 42.

*Primary Examiner*—Ralph A. Lewis
*Attorney, Agent, or Firm*—Cooley Godward LLP

[57] ABSTRACT

The present invention describes a novel composition and system for use for removal of organic and inorganic materials from a variety of substrates, including a tooth surface, without damage occurring to the substrate. The disclosed composition comprises a friable abrasive particle which when propelled by a gas stream at a surface for a time sufficient departs adequate energy to remove organic and inorganic materials from the surface without causing any significant ablation of the surface.

4 Claims, No Drawings

FRIABLE ABRASIVE MEDIA

CROSS-REFERENCE TO RELATED APPLICATIONS

This application is a continuation of U.S. patent application Ser. No. 08/647,686, filed May 13, 1996, now issued U.S. Pat. No. 5,810,587.

The present invention describes a novel composition and system for use for removal of organic and inorganic materials from a variety of substrates without damage occurring to the substrate. The disclosed composition comprises a friable abrasive particle which when propelled by a gas steam at a surface for a time sufficient departs adequate energy to remove organic and inorganic materials from the surface without causing any significant ablation of the surface.

One area of use for this invention is within the field of dentistry, with particular value in the special of orthodontics. For years dentists have straightened and repositioned teeth with the use of tensioning wires affixed to teeth via attatchment brackets. As is will known in the art, brackets are commonly secured directly to the tooth with adhesive resins and cements. When the brackets are removed either intentionally such as at the end of the treatment, or unintentionally due to a bond failure, the adhesive components remain both on the tooth and the bracket. The adhesive is then removed from the tooth structure by mechanical means such as scraping, ultrasonic scaling, or grinding with a bur. These methods of resin removal are not only time consuming but can also be damaging to the tooth. As the curette or bur scrapes close to the tooth surface, gouges and scratches are almost always left in the enamel. When gouges or scrapes occur, additional time is spent trying to polish out the scratches and healthy enamel is necessarily removed. Even when the current techniques result in removal of the resin from the tooth surface without scratching the tooth, the enamel pellicle is never really cleaned. This failure to remove all matter from the pellicle can be aesthetically unpleasant and limit the effectiveness of tooth whitening.

After debonding a bracket, removing resin paste from a tooth is one problem. The next problem is resin removal from the bracket; that is if it is to be reused. For most metal brackets sandblasting with an instrument as in Fernwood, U.S. Pat. No. 4,941,298 with a commonly used alpha aluminum oxide or silicon carbide particle works well. For non-metallic or ceramic brackets having a specially fused silica bonding face, the hard aluminum oxide abrasive sandblasting will not work because it quickly removes the fused silica facing. The bracket then becomes useless unless a new silica facing is placed on the bracket. Sandblasting with the disclosed composition allows brackets treated with a silica facing to be cleaned for reuse and rebonded. A further orthodontic application is the sandblast cleaning of the adhesive residue remaining around the edges of brackets when they are first bonded onto the tooth. Prior to this invention, the excess residue would normally be scraped off the tooth and around the bracket with an instrument such as a curette.

A further dental use is found for the simple and non damaging removal of temporary resins and cements from tooth structure.

A still further use in the field of dentistry is suggested for expediting the whitening of teeth. Teeth whitening in dentistry is generally performed by applying a whitening chemical for a period of time. The invention described herein speeds teeth whitening by removing all organic and inorganic contaminants in the tooth enamel pellicle thereby aiding in the delivery of the tooth whitening agent directly to the tooth. Various other examples for application in dentistry are envisioned where it is desirous to remove any organic or inorganic material from the tooth structure without damaging the tooth structure.

A still yet further dental use is within the area of implant dentistry. Implants are sometimes coated with a biocompatible coatings such as hydroxyapatite or alternatively a silica coating. The disclosed composition and system for use cleans debris from the coated implants without removing the coatings.

Outside the field of dentistry, the disclosed invention may be used for a variety of other applications. In the field of commercial painting, the invention discloses an improved way of paint removal without damaging the underlying structure. Other applications are found in the areas of art restoration, jewelry work and fossil restoration where organic and inorganic contaminants are to be removed without resultant damage to the underlying structure. Another application is found in the removal of contaminants on electronic components such as cleaning computer drive disk whether optical, floppy or metallic removal of masking material on silicon wafers, or circuit boards.

PRIOR ART

In the field of dentistry various methods exist which attempt to solve the problems previously discussed. For cleaning of organic and inorganic materials from tooth enamel sandblasting with "soft" (Dolomite, Moh hardness 4 to 6 instead of 8 or 9 for Alpha Alumina) insoluble abrasive through sandblasting means was disclosed by Black, U.S. Pat. No. 3,972,123; thereafter, Gallant, U.S. Pat. No. 4,174,571 proposed using soluble abrasives, particularly sodium bicarbonate, through sandblasting means to clean teeth. Although the latter approach is still commercially utilized, the system is inherently erosive to tooth structure and care must be used to avoid removing excessive tooth structure during cleaning procedures. These systems are generally not used for resin adhesive removal but rather for stain removal and general tooth cleaning.

For removing resin adhesives during orthodontic procedures, or for inlays/onlay cement removal, devices such as those disclosed in Black and Gallant, have been used with little or no success, rather devices commonly referred to as ultrasonic scalers such as the Cavitron by Dentsply, dental burrs or simply hand instruments such as scrapers, are the commonly used means. The later devices do successfully remove the resinous materials, however significant care must be used to avoid severe erosion occurring to the tooth structure. Further, resin removal by hand instruments are relatively slow and time consuming.

For applications other than dentistry, sandblasting with plastic and other pliant abrasive media, Lynn, U.S. Pat. No. 5,207,034 has been known to provide a means of removing organic and inorganic materials such as paint from structures without damaging the underlying structure. Two of the limitations of the plastic media methods known to the inventors have been the commercial price and the potential toxicity.

SPECIFICATION

Described more fully herein is a friable abrasive composition and system for its use for removing organic and inorganic materials from a substrate. Commonly used sandblasting abrasive media such as alpha aluminum oxide, silicon carbide and others generally are categorized as solid, homogeneous, relatively non-friable abrasives and range in hardness from 6 to 10 on the Moh hardness scale. The Moh index is one of the relative indexes used to indicate relative hardness. Moh 1 is characterized as extremely soft whereas Moh 10 which is specified as diamond is the hardest material known. These abrasives range in hardness depending upon the desired result and work performed by transferring the kinetic energy of the accelerated particles to the surface. The physics of sandblasting with particles as just described (aluminum oxide, silicon carbide) is simply a chipping and fracturing of a surface by high-speed particles impinging upon it. As long as the impinging particles are as hard or harder than the surface they're hitting, ablation will occur along with removal of any surface contaminats. There are at least five physical characteristics of an abrasive that affect its performance as a sandblasting medium; 1) particle velocity, 2) particle mass, 3) particle shape, 4) hardness, and 5)toughness also some times referred to as friability. Just as there are abrasion controlling characteristics of the propelled abrasive particles, so there are concomitant characteristics of the abraded surface which greatly affect the outcome. The factors include; 1)hardness, 2)surface toughness and 3)surface malleability.

The physical mechanism of sandblasting with the novel particles described herein varies widely from traditional sandblasting operations. The following generally describes the unique and patentable operation of the disclosed composition and system for use. The disclosed composition is comprised of large (10 to 200 micron) "snowball" like spheres. Like a snowball, the spheres are comprised of hundreds to thousands of tiny (0.01 to 5 micron) particles. The tiny particles are loosely bound together, allowing the spheres to crumble when they impinge upon their targeted surface. As a result of this impact crumbling, three mechanisms are observed. First, the spheres break apart and the tiny particles splay over a finite area as they disjoin. Second, each tiny particle quickly loses its kinetic energy as the splaying-out process continues. Unlike traditional sandblasting, there is essentially no bounce back by the spheres as compared to traditional abrasive media of comparable size and hence the bulk of their kinetic energy is transferred to the targeted surface rather than conserving their kinetic energy and rebounding. This is the significant difference between traditional sandblasting with hard, non-friable particles and sandblasting with the spheres described herein. Lastly, the energy transfer to the surface shows up as heat. Experimentally, we measured surface temperature increases in the range of 25 degrees Celsius. This heat transfer is extremely significant when the desired material to be removed is heat sensitive, such as may be the case with a dental resin. Experimentally, we observed that the outer surface of a dental adhesive or resin will slightly soften with this instantaneous but tiny amount of heat and pieces of it will dislodge quickly. As each successive sphere strikes during sandblasting, the adhesive/resin surface is softened and removed. When the last of the resin/adhesive is removed from the tooth enamel, we noted experimentally and confirmed by scanning electron microscopy that essentially no ablation of the tooth surface occurs at pressures as high as 200 psi for periods in excess of two minutes. Two reasons are thought to explain this phenomena; first, the tooth enamel, Moh hardness 4.5 is harder than the spheres, Moh hardness 3.5 and secondly, the convection cooling offsets the heat imparted to the enamel. When we used Dolomite (Moh hardness 3.5), a traditional abrasive, with similar hardness we were able to remove the dental resin however we noticed some tooth enamel erosion. The importance of having an abrasive which will not damage the underlying structure is particularly important in the field of dentistry where by law only the dentist is able to perform procedures which involve tooth structure removal. With the disclosed composition, a dentists assist can remove dental resins without fear of tooth structure damage.

We have observed a similar phenomena when we used the disclosed abrasive on temporary resin cement attached to tooth dentin as opposed to tooth enamel. In general the tooth enamel hardness is 4.5 on the Moh hardness scale as compared to dentin which is 2.5 on the Moh hardness scale. After the temporary resin cement is removed from the dentin, we did however observe slight ablation of the dentin after two minutes of sandblasting at pressures up to 200 psi. The slight ablation is believed to have occurred because the disclosed abrasive is slightly harder than the tooth dentin. Based upon the observed dentin ablation, it is important to offer multiple hardnesses of the disclosed friable abrasive to eliminate any potential dentinal damage. The method of varying sphere hardness is hereinafter disclosed.

Sphere hardness can be modified somewhat to allow softer or harder materials to be efficiently cleaned. To illustrate, we performed paint removal on two different metals, aluminum and steel. We choose a non-alloyed aluminum having a hardness of 2 to 2.9 Moh and a steel with a hardness of approximately 5 Moh We applied the same enamel paint to both surfaces. After the paint was dry we removed the paint with the disclosed composition (3.5 Moh). We observed no damage to the steel structure and only very minor ablation of the aluminum structure. We then did the same test with Dolomite (3.5 Moh) and observed minor ablation of the steel and moderate to severe ablation of the aluminum. Thereafter we used a slightly softer, Moh 3.0 variant of the disclosed composition and still observed no damage to the steel and now observed even less damage to the aluminum. Their was no observed time differential between the Moh 3.5 and Moh 3.0 compositions to remove the paint. Based upon our experimentation, the disclosed system is particularly effective with heat sensitive contaminants, such as resins, plastics, paints. All of the various applications can not possible be discussed herein, and those trained in the various relevant arts will observe additional consistent uses.

Spheres of the agglomerated small particles may be chosen from the group of aluminum trihydrates, such as gibbsite, bayerite and nordstrandite. These naturally occurring minerals when ground and sized in the range of 10 to 200 micron spheres will work effectively for the novel system disclosed. The raw material, for example gibbsite, may be ground and sized to a specific particle micron range (0.01 to 5 micron). It is then pressed into a cake and sintered at a temperature below the transition point or below the point where water of hydration is lost. The cake is then reground and sized into spheres ranging in size between 10 and 200 microns for packaging and shipping. Variations of this basic process could involve adding water or a binder after the first grinding. In this case, the sintering step might be altered or even eliminated. For dental applications, gibbsite works well but is not the only choice. Any small particle abrasive that can be processed into spheres and with a hardness less than Moh 4.0 would produce the same effect. Choices include dicalcium phosphate, gypsum, calcium carbonate, dolomite, as well as many other suitable similar particles. Aluminum Trihydrates made from Gibbsite are commercially available from Alcoa as plastic and paper fillers and work suitably for the disclosed system. Spheres made from other minerals are not known to be commercially available. The novel compositions disclosed herein are the manufacture of spheres other than aluminum trihydrates comprising a plurality of tiny particles bound together to form larger sphere like particle with varying hardness. The aluminum trihydrates range in hardness between 2.5 and 3.5 Moh. Spheres with differing desired hardness can be constructed out of suitable 0.01 to 5 micron particles generally having a hardness equal or up to 5 Moh less than the targeted structure. The constituent particles however may vary greatly in hardness depending upon desired ablation levels to the targeted structure.

In order to remove materials faster and where some moderate level of ablation is permissible, the disclosed composition may be mixed with traditional abrasive media such as alpha aluminum oxide.

When the spheres disjoin upon impact with the targeted surface, the tiny constituent particles cause a small dust cloud. The dust created is messy and unpleasant. Consequently, it is envisioned that a particle evacuation means operate concurrently to the sandblasting to allow for more pleasant and efficient system.

What the invention claimed is:

1. A method for removal of organic and inorganic matter from the surface of a tooth with minimal removal of the tooth enamel from the tooth surface, which method comprises creating a fluid stream laden with a friable abrasive composition comprising a plurality of sphere-shaped particles of 10 to 200 microns in size, wherein the sphere-shaped particles comprise a plurality of particles of 0.01 to 5 microns in size loosely bound together, directing the friable abrasive laden stream towards the tooth surface for a time sufficient so that the stream impinges upon the tooth surface and the large particles crumble, allowing the smaller particles to splay over the tooth surface, thereby removing the organic or inorganic material from the tooth surface.

2. The invention of claim 1, wherein said friable abrasive is an aluminum trihydrate.

3. The process of claim 1 wherein the particles are selected from the group of inorganic materials having a hardness equal to or up to 5 Moh hardness levels less than the targeted surface.

4. A composition of matter for removal of organic and inorganic materials from a tooth surface comprising:

a friable abrasive composition comprising a plurality of particles sized between 0.01 and 5 microns loosely bound together to form larger, sphere-shaped particles sized between 10 and 200 microns, which larger particles crumble when they are directed against a tooth surface.

* * * * *